(12) United States Patent
Kotani et al.

(10) Patent No.: US 7,510,833 B2
(45) Date of Patent: Mar. 31, 2009

(54) METHOD FOR EXAMINING OBESITY OR LEANNESS

(75) Inventors: Hidehito Kotani, Tsukuba (JP); Hiraku Itadani, Tsukuba (JP); Hiromitsu Araki, Tsukuba (JP); Kazuhiko Takahashi, Tsukuba (JP); Satoshi Mashiko, Tsukuba (JP); Akane Ishihara, Tsukuba (JP); Akio Kanatani, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 5 days.

(21) Appl. No.: 10/548,772

(22) PCT Filed: Mar. 12, 2004

(86) PCT No.: PCT/JP2004/003452

§ 371 (c)(1),
(2), (4) Date: Jun. 19, 2006

(87) PCT Pub. No.: WO2004/092368

PCT Pub. Date: Oct. 28, 2004

(65) Prior Publication Data

US 2007/0031833 A1    Feb. 8, 2007

(30) Foreign Application Priority Data

Mar. 13, 2003 (JP) .............................. 2003-067759
Jul. 31, 2003 (JP) .............................. 2003-204354

(51) Int. Cl.
*C12Q 1/68* (2006.01)
*C07H 21/04* (2006.01)
*C12P 19/34* (2006.01)

(52) U.S. Cl. .......................... 435/6; 536/24.3; 435/91.2
(58) Field of Classification Search .................. 435/6; 536/24.3
See application file for complete search history.

(56) References Cited

OTHER PUBLICATIONS

Gerhardt et al Molecular and Cellular endocrinology (2001) vol. 175, pp. 81-92.*
Sartipy et al (Proceedings the National Academy of Sciences USA, (2003) vol. 100, pp. 7265-7270, Epub May 19, 2003).*
Lemos et al (Circulation (2003) vol. 107, pp. 690-695.*
Genecard for MCP-1 (CCL2 GC17P029606, 2007, pp. 1-11.*
Herder et al (European Journal of Endocrinology (2006) vol. 154, 311-317).*
Vandesompele et al (Genome Biology (2002) vol. 3 , pp. 1-11.*
Cheung et al (Nature Genetics, 2003, vol. 33, pp. 422-425).*
Wu (Journal of Pathology, 2001, vol. 195, pp. 53-65).*
Newton et al (Journal of Computational Biology, 2001, vol. 8, pp. 37-52).*
Greenbaum et al (Genome Biology 2003, vol. 4, article 117, pp. 1-8).*
Bouloumie, A. et al. (1999) "Leptin induces oxidative stress in human endothelial cells" FASEB J. 13:1231-1238.
Cushing, S.D. et al. (1990) "Minimally modified low density lipoprotein induces monocyte chemotactic protein 1 in human endothelial cells and smooth muscle cells" PNAS USA 87:5134-5138.
Furutani, Y. et al. (1989) "Cloning and sequencing of the cDNA for human monocyte chemotactic and activating factor (MCAF)" Biochemical and Biophysical Research Communications 159:249-255.
Gerhardt, C.C. et al. (2001) "Chemokines control fat accumulation and leptin secretion by cultured human adipocytes" Molecular and Cellular Endocrinology 175: 81-92.
Koch, A.E. et al. (1992) "Enhanced production of monocyte chemoattractant protein-1 in rheumatoid arthritis" The Journal of Clinical Investigation, Inc. 90:772-779.
Stahl, R.A.K. et al. (1993) "Increased expression of monocyte chemoattractant protein-1 in anti-thymocyte antibody-induced glomerulonephritis" Kidney International 44:1036-1047.
Yamagishi, S. et al. (2001) "Leptin induces mitochondrial superoxide production and monocyte chemoattractant protein-1 expression in aortic endothelial cells by increasing fatty acid oxidation via protein kinase A" The Journal of Biological Chemistry 276:25096-25100.
Yoshimura, T. et al. (1989) "Human monocyte chemoattractant protein-1 (MCP-1) full-length cDNA cloning, expression in mitogen-stimulated blood monomuclear leukocytes, and sequence similarity to mouse competence gen JE" FEBS Letters 244: 488-493.
Gerhardt et al., "Chemokines control fat accumulation and leptin secretion by cultured human adipocytes," *Molecular and Cellular Endocrinology*, 175(1-2):81-92 (2001).

* cited by examiner

*Primary Examiner*—Ram R Shukla
*Assistant Examiner*—Steven C Pohnert
(74) *Attorney, Agent, or Firm*—Richard C. Billups; Catherine D. Fitch

(57) ABSTRACT

In the examination of obesity or leanness, the examination is based on the expression level of the MCP-1 gene or the MCP-1 protein in a tissue or cell analyte, or on the polymorphism in the gene. In the evaluation of compounds, including screening for therapeutic agents for obesity or leanness, the properties of the MCP-1 gene or the MCP-1 protein are utilized to carry out the evaluation.

1 Claim, 6 Drawing Sheets

SEQUENCE LISTING

<160> NUMBER OF SEQ ID NOS: 12

<210> SEQ ID NO 1
<211> LENGTH: 28
<212> TYPE: DNA

```
<213> ORGANISM: Artificial
<220> FEATURE:
<223> OTHER INFORMATION: TaqMan Probe for murine MCP-1

<400> SEQUENCE: 1
ccactcacct gctgctactc attcacca                                          28

<210> SEQ ID NO 2
<211> LENGTH: 21
<212> TYPE: DNA
<213> ORGANISM: Artificial
<220> FEATURE:
<223> OTHER INFORMATION: mMCP1-69F

<400> SEQUENCE: 2
tcagccagat gcagttaacg c                                                 21

<210> SEQ ID NO 3
<211> LENGTH: 23
<212> TYPE: DNA
<213> ORGANISM: Artificial
<220> FEATURE:
<223> OTHER INFORMATION: mMCP1-163R

<400> SEQUENCE: 3
tgatcctctt gtagctctcc agc                                               23

<210> SEQ ID NO 4
<211> LENGTH: 28
<212> TYPE: DNA
<213> ORGANISM: Artificial
<220> FEATURE:
<223> OTHER INFORMATION: TaqMan Probe for murine beta-actin

<400> SEQUENCE: 4
cctgaggctc ttttccagcc ttccttct                                          28

<210> SEQ ID NO 5
<211> LENGTH: 19
<212> TYPE: DNA
<213> ORGANISM: Artificial
<220> FEATURE:
<223> OTHER INFORMATION: mMCP1-F

<400> SEQUENCE: 5
tattggcaac gagcggttc                                                    19

<210> SEQ ID NO 6
<211> LENGTH: 21
<212> TYPE: DNA
<213> ORGANISM: Artificial
<220> FEATURE:
<223> OTHER INFORMATION: mMCP1-R

<400> SEQUENCE: 6
atgccacagg attccatacc c                                                 21

<210> SEQ ID NO 7
<211> LENGTH: 19
<212> TYPE: DNA
<213> ORGANISM: Artificial
<220> FEATURE:
<223> OTHER INFORMATION: mMCP1-26F

<400> SEQUENCE: 7
cctgctgttc acagttgcc                                                    19
```

<210> SEQ ID NO 8
<211> LENGTH: 21
<212> TYPE: DNA
<213> ORGANISM: Artificial
<220> FEATURE:
<223> OTHER INFORMATION: mMCP1-440R

<400> SEQUENCE: 8

```
cactgtcaca ctggtcactc c                                              21
```

<210> SEQ ID NO 9
<211> LENGTH: 757
<212> TYPE: DNA
<213> ORGANISM: Homo sapiens
<220> FEATURE:
<221> NAME/KEY: CDS
<222> LOCATION: (72)..(371)
<220> FEATURE:
<221> NAME/KEY: sig_peptide
<222> LOCATION: (72)..(140)

<400> SEQUENCE: 9

```
ggaaccgaga ggctgagact aacccagaaa catccaattc tcaaactgaa gctcgcactc      60
tcgcctccag c atg aaa gtc tct gcc gcc ctt ctg tgc ctg ctg ctc ata     110
            Met Lys Val Ser Ala Ala Leu Leu Cys Leu Leu Leu Ile
              1               5                  10 gca gcc acc ttc att ccc caa ggg ctc gct cag cca gat gca atc aat     158
Ala Ala Thr Phe Ile Pro Gln Gly Leu Ala Gln Pro Asp Ala Ile Asn
 15                  20                  25 gcc cca gtc acc tgc tgt tat aac ttc acc aat agg aag atc tca gtg     206
Ala Pro Val Thr Cys Cys Tyr Asn Phe Thr Asn Arg Lys Ile Ser Val
30                  35                  40                  45 cag agg ctc gcg agc tat aga aga atc acc agc agc aag tgt ccc aaa     254
Gln Arg Leu Ala Ser Tyr Arg Arg Ile Thr Ser Ser Lys Cys Pro Lys
                 50                  55                  60 gaa gct gtg atc ttc aag acc att gtg gcc aag gag atc tgt gct gac     302
Glu Ala Val Ile Phe Lys Thr Ile Val Ala Lys Glu Ile Cys Ala Asp
             65                  70                  75 ccc aag cag aag tgg gtt cag gat tcc atg gac cac ctg gac aag caa     350
Pro Lys Gln Lys Trp Val Gln Asp Ser Met Asp His Leu Asp Lys Gln
         80                  85                  90 acc caa act ccg aag act tga acactcactc cacaacccaa gaatctgcag          401
Thr Gln Thr Pro Lys Thr
     95 ctaacttatt tcccctagc tttccccaga caccctgttt tattttatta taatgaattt      461 tgtttgttga tgtgaaacat tatgccttaa gtaatgttaa ttcttattta agttattgat     521 gttttaagtt tatctttcat ggtactagtg tttttagat acagagactt ggggaaattg      581 cttttcctct tgaaccacag ttctaccct gggatgtttt gagggtcttt gcaagaatca      641 ttaatacaaa gatttttttt taacattcca atgcattgct aaaatattat tgtggaaatg     701 aatatttgt aactattaca ccaataaat atattttgt acaaaaaaaa aaaaaa           757
```

<210> SEQ ID NO 10
<211> LENGTH: 99
<212> TYPE: PRT
<213> ORGANISM: Homo sapiens

<400> SEQUENCE: 10

```
Met Lys Val Ser Ala Ala Leu Leu Cys Leu Leu Leu Ile Ala Ala Thr
  1               5                  10                  15
```

```
Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
         35                  40                  45

Ala Ser Tyr Arg Arg Ile Thr Ser Ser Lys Cys Pro Lys Glu Ala Val
     50                  55                  60

Ile Phe Lys Thr Ile Val Ala Lys Glu Ile Cys Ala Asp Pro Lys Gln
 65                  70                  75                  80

Lys Trp Val Gln Asp Ser Met Asp His Leu Asp Lys Gln Thr Gln Thr
                 85                  90                  95

Pro Lys Thr

<210> SEQ ID NO 11
<211> LENGTH: 584
<212> TYPE: DNA
<213> ORGANISM: Mus musculus
<220> FEATURE:
<221> NAME/KEY: CDS
<222> LOCATION: (89)..(535)
<220> FEATURE:
<221> NAME/KEY: sig_peptide
<222> LOCATION: (89)..(157)

<400> SEQUENCE: 11
agtgcagaga gccagacggg aggaaggcca gcccagcacc agcaccagcc aactctcact      60
gaagccagct ctctcttcct ccaccacc atg cag gtc cct gtc atg ctt ctg       112
                              Met Gln Val Pro Val Met Leu Leu
                                1               5 ggc ctg ctg ttc aca gtt gcc ggc tgg agc atc cac gtg ttg gct cag      160
Gly Leu Leu Phe Thr Val Ala Gly Trp Ser Ile His Val Leu Ala Gln
         10                  15                  20 cca gat gca gtt aac gcc cca ctc acc tgc tgc tac tca ttc acc agc      208
Pro Asp Ala Val Asn Ala Pro Leu Thr Cys Cys Tyr Ser Phe Thr Ser
 25                  30                  35                  40 aag atg atc cca atg agt agg ctg gag agc tac aag agg atc acc agc      256
Lys Met Ile Pro Met Ser Arg Leu Glu Ser Tyr Lys Arg Ile Thr Ser
                 45                  50                  55 agc agg tgt ccc aaa gaa gct gta gtt ttt gtc acc aag ctc aag aga      304
Ser Arg Cys Pro Lys Glu Ala Val Val Phe Val Thr Lys Leu Lys Arg
             60                  65                  70 gag gtc tgt gct gac ccc aag aag gaa tgg gtc cag aca tac att aaa      352
Glu Val Cys Ala Asp Pro Lys Lys Glu Trp Val Gln Thr Tyr Ile Lys
         75                  80                  85 aac ctg gat cgg aac caa atg aga tca gaa cct aca act tta ttt aaa      400
Asn Leu Asp Arg Asn Gln Met Arg Ser Glu Pro Thr Thr Leu Phe Lys
     90                  95                 100 act gca tct gcc cta agg tct tca gca cct ttg aat gtg aag ttg acc      448
Thr Ala Ser Ala Leu Arg Ser Ser Ala Pro Leu Asn Val Lys Leu Thr
105                 110                 115                 120 cgt aaa tct gaa gct aat gca tcc act acc ttt tcc aca acc acc tca      496
Arg Lys Ser Glu Ala Asn Ala Ser Thr Thr Phe Ser Thr Thr Thr Ser
                125                 130                 135 agc act tct gta gga gtg acc agt gtg aca gtg aac tag tgtgactcgg       545
Ser Thr Ser Val Gly Val Thr Ser Val Thr Val Asn
                140                 145 actgtgatgc cttaattaat attaaactta tttaactta                           584

<210> SEQ ID NO 12
<211> LENGTH: 148
```

```
<212> TYPE: PRT
<213> ORGANISM: Mus musculus

<400> SEQUENCE: 12

Met Gln Val Pro Val Met Leu Leu Gly Leu Leu Phe Thr Val Ala Gly
1               5                   10                  15

Trp Ser Ile His Val Leu Ala Gln Pro Asp Ala Val Asn Ala Pro Leu
            20                  25                  30

Thr Cys Cys Tyr Ser Phe Thr Ser Lys Met Ile Pro Met Ser Arg Leu
        35                  40                  45

Glu Ser Tyr Lys Arg Ile Thr Ser Ser Arg Cys Pro Lys Glu Ala Val
    50                  55                  60

Val Phe Val Thr Lys Leu Lys Arg Glu Val Cys Ala Asp Pro Lys Lys
65                  70                  75                  80

Glu Trp Val Gln Thr Tyr Ile Lys Asn Leu Asp Arg Asn Gln Met Arg
                85                  90                  95

Ser Glu Pro Thr Thr Leu Phe Lys Thr Ala Ser Ala Leu Arg Ser Ser
            100                 105                 110

Ala Pro Leu Asn Val Lys Leu Thr Arg Lys Ser Glu Ala Asn Ala Ser
        115                 120                 125

Thr Thr Phe Ser Thr Thr Thr Ser Ser Thr Ser Val Gly Val Thr Ser
    130                 135                 140

Val Thr Val Asn
145
```

METHOD FOR EXAMINING OBESITY OR LEANNESS

RELATED APPLICATION

This application is the U.S. national phase under 35 U.S.C. § 371 of International Application No. PCT/JP2004/003452, filed Mar. 12, 2004.

TECHNICAL FIELD

This invention relates to a method for examining obesity or leanness utilizing the gene or protein of MCP-1 (monocyte chemoatractant protein-1: monocyte chemotaxis factor) and to a diagnostic agent comprising the gene or the protein. This invention also relates to a method for evaluating a compound to be effective for the treatment or prevention of obesity or leanness utilizing the gene or the protein.

BACKGROUND ART

Obesity is the risk factor for various adult diseases that are represented by hypertension, diabetes, hyperlipemia, ischemic heart disease, and others. Since many of them are chronic disorders, they are believed to cause an escalation in the medical cost in the future and are becoming a big social problem.

Adequate examination and identification of such obesity condition is indispensable to the proper treatment that follows. Hence, there has always been a need to uncover convenient and highly accurate obesity markers. In recent years, it has also been beginning to be recognized that the genotype, such as genetic polymorphism, of a recipient of a drug influences the efficacy of the administered drug. Markers for examination or diagnosis at molecular levels have been desired in the clinical tests at the development stages of drugs or in the so-called tailored medication.

Under these circumstances BMI (Body Mass Index: body weight (kg)/height (m)/height (m)) is principally used as a maker for obesity. The present situation is thus such that there are hardly known any markers capable of diagnosis at molecular levels such as gene or protein.

MCP-1 is a protein whose open reading frame consist of 99 amino acids (in the case of human) and which belongs to the CC chemokine subfamily (Accession No. human NM002982 (SEQ ID NO:9 and NO:10)), murine NM011333 (SEQ ID NO:11 and NO:12)). MCP-1 was cloned in 1989 (Yoshimura T. et al., FEBS Letters, 244, 487-493 (1989); Furutani Y. et al., Biochem. Biophys. Res. Commun., 159, 249-255 (1989)) and was later implicated to be related with arteriosclerosis, rheumatoid arthritis and nephritis (Proc. Natl. Acad. Sci. USA, 87, 5134-5138 (1990); J. Clin. Invest. 90, 772-779 (1992); Kidney Int. 44, 1036-1047 (1993)).

Chemokines are a group of proteins having migration activity toward leukocytes. It has become clear that they are involved in the pathological onset, progress, and animus of inflammation at its acute and chronic stages. Particularly, it is known that MCP-1 possesses potent chemotaxis and activation action toward monocytes. It is, thus, thought that MCP-1 can be used in the utility of immunoactivation action, antitumor action and the like.

As stated above, a number of findings on MCP-1 have been reported, and it is known that MCP-1 is responsible for diverse life phenomena in the living body. However, concerning the relationship between MCP-1 and obesity, there were only a report that the expression level of MCP-1 was elevated when leptin, which was known as a satiety factor, was administered to certain cells (FASEB J., 13, 1231-1238 (1999); J. Biol. Chem., 276, 25096-25100 (2001)) and a report suggesting that the stimulation by chemokines was indirectly involved in the accumulation of fat (Molecular and cellular Endocrin., 175, 81-92 (2001)). The direct relationship between MCP-1 and obesity as well as the correlation between the expression level of MCP-1 and obesity or body weight changes has not been known at all.

DISCLOSURE OF THE INVENTION

This invention has been made in view of the problems inherent in the prior art as mentioned above; and it aims at providing a method for examining obesity or leanness which can be judged at a molecular level and a diagnostic agent for obesity or leanness utilizing the molecule. It is also an object of the invention to provide a method for evaluating a compound such as screening for therapeutic agent for obesity or leanness, as well as to provide compounds that have been evaluated as effective for obesity or leanness by the method of evaluation.

As a result of repeating intensive investigations to accomplish the above objects, the present inventors found that a certain correlation existed between the expression amount or blood concentrations of MCP-1 and body weight change, upon which this invention has been completed.

Specifically, the method for examining obesity or leanness according to this invention is characterized in determining the expression level of the MCP-1 gene in a tissue or cell analyte. In other words, examination of the degree of obesity will be possible based on the expression level of the MCP-1 gene. It is, then, preferable to carry out the determination of the expression level with the aid of a DNA microarray.

Also, the method for examining obesity or leanness according to this invention is characterized in determining the expression level of the MCP-1 protein in a tissue or cell analyte. In other words, examination of the degree of obesity will be possible based on the expression level of the MCP-1 protein.

Further, the method for examining obesity or leanness according to this invention is characterized in detecting any change in the expression level of the MCP-1 gene in a tissue or cell analyte. Specifically, there is provided a method for examining or predicting the degree of obesity comprising comparing an initial value of the expression level of the MCP-1 gene with a determined value of the expression level after a prescribed period (e.g., the difference between or the ratio of the initial value to the determined value). It is, then, preferable to carry out the determination of the expression levels with the aid of a DNA microarray.

Also, the method for examining obesity or leanness according to this invention is characterized in detecting any change in the expression level of the MCP-1 protein in a tissue or cell analyte. Specifically, there is provided a method for examining or predicting the degree of obesity comprising comparing an initial value of the expression level of the MCP-1 protein with a determined value of the expression level after a prescribed period (e.g., the difference between or the ratio of the initial value to the determined value).

Also, the method for examining obesity or leanness according to this invention is characterized in detecting polymorphism existing in the MCP-1 gene in a tissue or cell analyte. In other words, the examination or prediction of the degree of obesity will be possible based on the genetic polymorphism of the MCP-1 gene.

Further, the method for examining obesity or leanness according to this invention is characterized in detecting the expression amount or the activity of a protein that influences the expression amount of the MCP-1 gene through interaction with the MCP-1 protein. In other words, the examination or prediction of the degree of obesity will be possible based on the expression amount or the activity of a protein that influences the expression amount of the MCP-1 gene.

Also, the diagnostic agent for obesity or leanness according to this invention is characterized in containing as an active ingredient, an antibody against the MCP-1 protein.

Furthermore, the diagnostic kit for obesity or leanness according to this invention is characterized in containing an antibody against the MCP-1 protein. Preferably, the kit contains a fluorescent substance to detect the antibody (primary antibody) or a secondary antibody labeled with a radioisotope and a buffer for use in the antigen-antibody reaction.

Also, the method for evaluating a compound to be effective for the treatment or prevention of obesity or leanness according to this invention is characterized in comprising the steps of: administering to or contacting with an animal or cell subject, a compound to be assayed; and establishing whether the compound modulates the expression level of the MCP-1 gene or a gene that is functionally equivalent thereto in the animal or cell.

Further, the method for evaluating a compound to be effective for the treatment or prevention of obesity or leanness according to this invention is characterized in comprising the steps of administering to or contacting with an animal or cell subject, a compound to be assayed; and establishing whether the compound modulates the expression level of the MCP-1 protein or a protein that is functionally equivalent thereto in the animal or cell.

Still further, the method for evaluating a compound to be effective for the treatment or prevention of obesity or leanness according to this invention is characterized in comprising the steps of contacting a compound to be assayed with the MCP-1 protein; and establishing whether the compound influences the activity of the protein.

The compound according to this invention is characterized in that it has been evaluated as effective for the treatment or prevention of obesity or leanness by the method of evaluating a compound according to the invention.

BEST MODE FOR CARRYING OUT THE INVENTION

Figure 1:
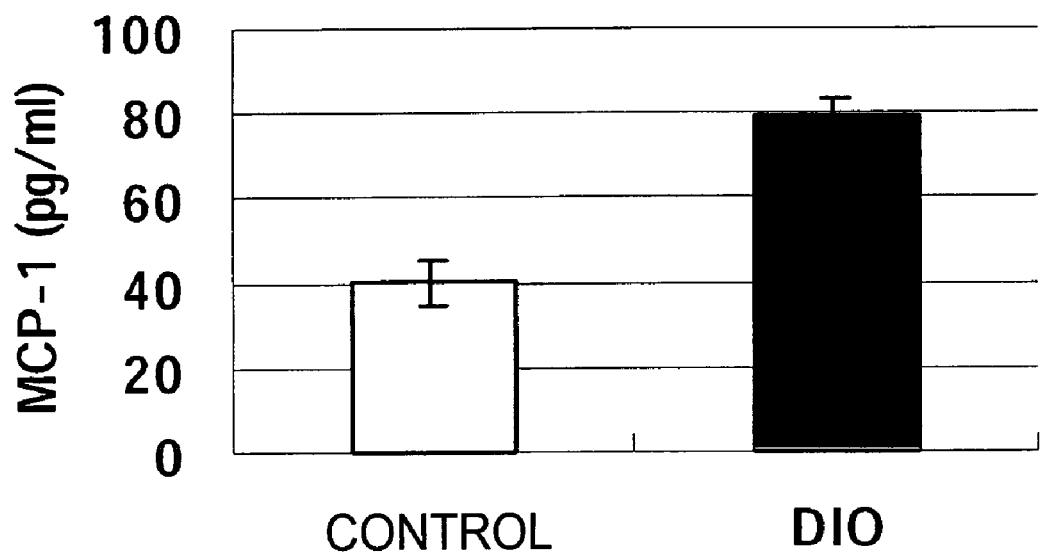
FIG. 1 is a graph comparing the blood concentrations of MCP-1 between DIO mice and the control group.

The preferred embodiments of this invention will be described in detail hereinafter.

In this invention, "expression level" refers to the absolute or relative amount of a transcription product of the MCP-1 gene. Here, the gene includes both of DNA and mRNA. When the object to be detected in expression is a protein, the "expression level" refers to the absolute or relative amount of a translational product of the MCP-1 gene.

In this invention, "MCP-1 protein" includes both of a precursor protein having a signal peptide and a mature protein having no signal peptide, but preferably refers to the mature protein. For example, human MCP-1 protein can be either a precursor protein comprising 99 amino acids (SEQ ID NO:10) with a signal peptide comprising 23 amino acids (amino acids No. 1 to No. 23 in SEQ ID NO:10) or a mature protein comprising 76 amino acids (amino acids No. 24 to No. 99 in SEQ ID NO:10) without the signal peptide. Murine MCP-1 protein can be either a precursor protein comprising 148 amino acids (SEQ ID NO:12) with a signal peptide comprising 23 amino acids (amino acids No. 1 to No. 23 in SEQ ID NO:12) or a mature protein comprising 125 amino acids (amino acids No. 24 to No. 148 in SEQ ID NO:12) without the signal peptide.

In this invention, "tissue analyte" is not particularly limited in its kind insofar as it is a tissue that can be extracted from the living body when the examination of obesity or leanness is performed. Preferably it is, for example, a liver tissue, a fat tissue, a muscle tissue or a blood tissue from the standpoint that the influence of obesity or leanness is likely reflected in each tissue. Also preferably, it is the blood tissue among the aforementioned tissues from the standpoint of the ease with which the tissue can be isolated. Here, there is no particular limitation to the animal species from which these tissues are derived. It is, however, preferred to be a human because the principle utility of this invention is a clinical use in humans.

In this invention, "cell analyte (or cell subject)" is not particularly limited in its kind insofar as it is a cell that can be extracted from the living body when the examination of obesity or leanness is performed. Preferably it is, for example, a liver cell, a fat cell (e.g., white adipocyte or brown adipocyte), a muscle cell (e.g., myoblast, skeletal muscle cell or smooth muscle cell), a pancreas cell (e.g., inslet cell), or a blood cell from the standpoint that the influence of obesity or leanness is likely reflected in each cell. Here, there is no particular limitation to the animal species from which these tissues are derived. It is, however, preferred to be a human because the principle utility of this invention is a clinical use in humans.

In this invention, "obesity" includes the so-called "obesity" accompanied by complications of diabetes or hypertension or by visceral fat, in addition to the general obesity that is defined as the condition in which fat tissues have excessively accumulated. In this invention, "obesity" also means a condition where the body weight has increased as compared to the original weight when the body weight control is effected by drug administration or the like.

On the other hand, in this invention "leanness" means a concept as opposed to the obesity just mentioned as well as means a condition where the body weight has decreased as compared to the original weight when the body weight control is effected by drug administration, dieting or the like.

In this invention, "examination" includes not only the case where obesity or leanness is simply judged, but also the case where obesity or leanness in the future is predicted.

(1) Method for Examining Obesity or Leanness According to this Invention (A) Method for Examining Obesity or Leanness by Determining the Expression Level of the MCP-1 Gene By detecting any change in the expression level of the MCP-1 gene in the aforesaid tissue or cell analyte, or alternatively by determining the expression level, it is possible to examine or diagnose whether the living body (such as a human) is obese or lean from which the tissue or cell analyte has been extracted. It is also possible not only to examine the condition of being obese or lean at the time of examination, but also to predict whether obesity or leanness will ensue in the future.

The specific methods for such examination will be described hereinafter.

The tissue or cell analyte is first extracted from the living body that will be subjected to examination. The extraction method is not particularly limited and the extraction can be carried out by known techniques.

The gene that will be subjected to the expression level determination is then prepared from the extracted tissue or cell analyte.

In determining the expression level of the MCP-1 gene, it is first necessary to prepare RNA (total RNA or mRNA) of MCP-1 from the tissue or cell analyte. Such preparation of RNA can be carried out according to known techniques and it may be done, for example, by referring to Molecular cloning A LABORATORY MANUAL 2nd EDITION (1989) (T. Maniatis: Cold Spring Harbor Laboratory Press) 7.3-7.36. The thus-prepared RNA can be used to determine its expression amount according to a gene amplification method such as RT-PCR, the technique utilizing a DNA microarray (e.g., DNA chip manufactured by Affymetrix Inc.) or Northern hybridization, for example. Alternatively, the tissue or cell analyte can be used to determine the expression amount according to in situ hybridization or the like.

In order to detect any change in the expression level of the MCP-1 gene, the determination of the expression amount mentioned above may be conducted before and after the period during which the expression amount has been predicted to change (e.g., before and after the administration of an anti-obesity drug) and the difference in the expression amount may be determined.

Specifically, if the expression level is significantly elevated in the tissue or cell analyte before and after the period during which the expression amount of the MCP-1 gene has been predicted to change as described above, diagnosis can be made that the body weight has increased or there is the possibility of its increase in the future. If, on the other hand, the expression level is significantly lowered, diagnosis can be made that the body weight has decreased or there is the possibility of its decrease in the future.

(B) Method for Examining Obesity or Leanness by Determining the Expression Level of the MCP-1 Protein By detecting any change in the expression level of the MCP-1 protein in the tissue or cell analyte, or alternatively by determining the expression level, it is possible to examine and/or diagnose whether the living body (such as a human) is obese or lean from which the tissue or cell analyte has been extracted. It is also possible not only to examine the condition of being obese or lean at the time of examination, but also to predict whether obesity or leanness will ensue in the future.

The specific methods for such examination will be described hereinafter.

The methods of determining the expression level of the protein include a method of quantifying the protein isolated from the living body and a method of determining the blood concentration of the protein. Thus, the methods are not particularly limited to those specific ones.

Specific examples of the method of quantifying the protein isolated from the living body are as what follow. The MCP-1 protein is first prepared from the tissue or cell analyte. Such preparation of the protein can be carried out according to known techniques and it may be done, for example, by the method as described in Proc. Natl. Acad. Sci. USA, 86, 1850-1854 (1989). The thus-prepared protein can be used to determine its expression amount according to the method utilizing a protein chip (e.g., the protein chip system manufactured by Ciphergen Biosystems Ltd.), or an immunological method (e.g., ELISA, EIA and Western blotting). Alternatively, the tissue or cell analyte can be used to determine the expression amount according to immunostaining or the like. On the other hand, specific examples of the method of determining the blood concentration of the protein include a method of quantifying the MCP-1 protein by the immunological technique mentioned above using the blood collected from the living body.

After the expression level of the MCP-1 gene or the MCP-1 protein is determined as described above, its results are analyzed, and thereby, the obesity or leanness of the subject can be examined. In other words, since it has become clear based on this invention that a certain correlation exists between the expression level of the MCP-1 protein and the body weight, the results from examination are compared with the expression amounts of the MCP-1 protein in the control group (normal subject, etc.) and thus it will be possible to judge the degree of obesity or leanness. Based on the method of examination according to this invention, it will also be possible not only to examine the condition of being obese or lean at the time of examination, but also to predict whether obesity or leanness will ensue in the future. This is due to the fact that the blood concentration of the MCP-1 protein notably tends to increase or decrease prior to an increase or decrease in the body weight. The present inventors have discovered that this tendency is strong with respect to the relationship between a decrease in the blood concentration of the MCP-1 protein and a decrease in the body weight.

In order to detect any change in the expression level of the MCP-1 protein, the determination of the expression amount mentioned above may be conducted before and after the period during which the expression amount has been predicted to change (e.g., before and after the administration of an anti-obesity drug) and the difference in the expression amount may be determined.

Specifically, if the expression level is significantly elevated in the tissue or cell analyte before and after the period during which the expression amount of the MCP-1 protein has been predicted to change as described above, diagnosis can be made that the body weight has increased or there is the possibility of its increase in the future. If, on the other hand, the expression level is significantly lowered, diagnosis can be made that the body weight has decreased or there is the possibility of its decrease in the future.

(C) Method for Examining Obesity or Leanness by Detecting genetic Polymorphism of the MCP-1 Gene When the genetic polymorphism exists in the MCP-1 gene, the expression level of the MCP-1 gene or the MCP-1 protein may change depending upon the type, the absence or presence of the polymorphism, or aberration may result in the activity of the protein. By detecting such genetic polymorphism, it is therefore possible to obtain information on the expression or the activity of MCP-1 and to examine whether the subject is obese or lean from which the tissue or cell analyte was derived. Specific examples of such genetic polymorphism include minisatellite, microsatellite and SNP (single nucleotide polymorphism).

The detection of polymorphism in the MCP-1 gene can be carried out in the manner described below. Specifically, the base sequence of a region in the MCP-1 gene that regulates its expression amount is determined in the targeted subject to be examined for obesity or leanness and the polymorphic site is then detected. The frequency of alleles in the polymorphic site detected is calculated; and the allele that has significantly increased or decreased in the subject population is detected to identify the polymorphism that is correlated to obesity or leanness. The genetic polymorphism thus detected can then be, for example, clinically detected in the genomic DNA derived from the subject by the analysis of the base sequence at the polymorphic site, by the method utilizing the difference in the physicochemical properties of DNA to be altered depending on the types of bases that are present in the polymorphic site or the difference in the restriction enzyme site, by the method utilizing a detection probe adapted to the detection of the polymorphic site, or by the method utilizing mass spectrometry.

(D) Method for Examining Obesity or Leanness by Detecting the Expression Amount or the Activity of a Protein that Influences the Expression Amount of the MCP-1 Gene Through Interaction with the MCP-1 Protein.

Many proteins interact with other proteins to exert their predetermined physiological functions in the living body. For example, it is known that the MCP-1 protein is produced in vascular endothelial cells or smooth muscle cells and accelerates its acceptor-CCR2 mediated chemotaxis of monocytes, lymphocytes, basophiles or the like. Therefore, a certain correlation exists between the MCP-1 protein and the expression amount or the activity of a protein that influences the expression amount of the MCP-1 gene through interaction with the MCP-1 protein. The correlation is thus such that if the behavior of one party is detected, the behavior of the other party can be predicted.

Herein, "interaction" refers to that the MCP-1 protein and another protein directly or indirectly induce action. For example, there are mentioned the action that produces amino acid modification or the like by the physical contact of the MCP-1 protein with another protein and the action that indirectly influences the expression of the MCP-1 protein through a third protein-mediated interaction. Such proteins include, for example, proteins that exert physiological functions at either downstream or upstream the MCP-1 protein in the signal transduction mediated by the MCP-1 protein. More specifically, there are CCR2 which is an acceptor of the MCP-1 protein and signal transducting molecules that are located downstream CCR2, for example. The method for examining the expression amount or the activity of a protein that is located upstream or downstream the MCP-1 protein may appropriately be selected from preferable means depending on the type of the targeted protein. The specific means are not particularly limited.

The methods for examining obesity or leanness according to this invention as described in (A) to (D) above enables not only the diagnosis of obesity or leanness at a molecular level, but also the prediction of the likelihood of becoming obese or lean in the future. As compared to the conventional diagnostic methods, a more accurate diagnosis will be possible.

(2) Diagnostic Agent or Kit for Obesity or Leanness

The expression amount of the MCP-1 protein bears a correlation with the change in the body weight resulting from obesity or leanness. Therefore, antibodies against the protein can be used to detect and determine the mass of the protein in the cell or tissue analyte, and thereby, the examination of obesity or leanness can conveniently be carried out. Here, "antibody" refers to the whole antibody molecule or its fragment capable of binding to any antigenic products of the MCP-1 gene. Such antibodies can be produced by known methods and may be either monoclonal antibodies or polyclonal antibodies. Known methods may be used as the immunological determination method relaying on the antibodies. Specifically, there are fluorescence antibody technique and enzyme-labeled antibody technique, for example.

A kit containing the antibody can also be prepared, which enables this invention to be practiced. The construction of the kit may be, for example, provided with a secondary antibody labeled with a fluorescent label or an isotope to detect the antibody, and a buffer for use in carrying out antigen-antibody reaction in addition to the antibody.

Based on the use of such diagnostic agent for obesity or leanness, it is possible not only to diagnose obesity or leanness at a molecular level, but also to predict the likelihood of becoming obese or lean in the future. As compared to the conventional diagnostic methods, a more accurate diagnosis will be possible. Based on the use of the diagnostic kit for obesity or leanness according to this invention, it is also possible to perform the accurate diagnosis as described above very conveniently.

(3) Method for Evaluating a Compound to be Effective for the Treatment or Prevention of Obesity or Leanness According to this Invention The evaluation of a compound to be assayed can be performed by administering to or contacting with an animal or cell subject the compound to determine the varying expression amounts of the MCP-1 gene or the MCP-1 protein, or by contacting the compound with the MCP-1 protein to investigate the effects that influence the activity of the protein.

In other words, it is thought that among such compounds to be assayed there are some which act on the cell or tissue to normalize or control the expression level of the MCP-1 gene or the MCP-1 protein or the activity of the MCP-1 protein and then to normalize the mechanism responsible for obesity or leanness, such as the accumulation of fats or the control of appetite. According to the methods of evaluation as will be described below, it will be possible to evaluate a compound to be effective as a therapeutic agent or effective in the prevention of obesity or leanness. Here, "evaluation" refers to a concept including not only screening for compounds, but also validation.

The present inventors have also discovered that the activation of monocytes, i.e., an increase of CD11b positive monocytes, is accelerated by the administration of MCP-1 to elevate its blood concentration. In the past, it was thought that MCP-1 was secreted from the inflammation site of blood vessel into the vessel and consequently, the activation of monocytes was accelerated. However, in addition to this the activation of monocytes is caused by MCP-1 from the outside of the blood vessel. The chemotaxis of monocytes is accelerated by their activation and the subsequent production of macrophages also results in arteriosclerosis. Thus, the increased MCP-1 by virtue of obesity can be a cause of arteriosclerosis.

Based on the method for evaluating compounds according to this invention, it will be possible to evaluate a compound to be effective for the treatment or prevention of obesity or leanness by using as an index, the expression level of the MCP-1 gene or the MCP-1 protein, or the activity of the MCP-1 protein. Likewise, it will be possible to evaluate a compound to be effective for the treatment or prevention of arteriosclerosis through obesity.

(A) Method for Evaluation Using as an Index, the Ability to Regulate the Expression Level of the MCP-1 Gene A compound to be assayed is administered to or contacted with an animal or cell subject to establish whether the compound modulates the expression level of the MCP-1 gene or a gene that is functionally equivalent thereto in the subject animal or cell. This allows the evaluation of an effective compound for the treatment or prevention of obesity or leanness.

Specifically, the evaluation of a compound to be assayed is carried out in the procedure below.

The compound to be assayed is first administered to or contacted with the animal or cell subject. Here, insofar as the compound to be assayed is a candidate compound for the therapeutic or preventive agents for obesity or leanness, its structure or properties do not matter and the type of compounds is non-limiting. The animal subjects include, for example, a mouse, rat, rabbit, dog and monkey.

The method of administering the compound to be assayed to the subject animal is not particularly limited. Specifically, there are oral administration and parental administration (such as transdermal administration, intramuscular injection, intravenous injection and subcutaneous injection), for example. The method of contacting the compound to be assayed with the cell subject is not particularly limited. Specifically, there is a method of mixing them in a buffer (e.g., phosphate buffer) to allow contact, for example.

Next, it is established whether the compound to be assayed modulates the expression level of the MCP-1 gene or a gene that is functionally equivalent thereto in the subject animal or cell.

The method of establishing the presence or the absence of modulation of the expression level of the gene is not particularly limited. The method can be performed by detecting any change in the expression amount of the gene as the control being prior to the administration or the contacting, according to a gene amplification technique such as RT-PCR, the technique utilizing a DNA microarray, or Northern hybridization. There may be used an animal or a cell into which the fused gene of the expression regulating region of the gene and a reporter gene has artificially been introduced. In this instance, the reporter genes specifically include a β-glactosidase gene, a luciferase gene and a green fluorescent protein gene, for example.

Herein, "gene that is functionally equivalent to the MCP-1 gene" refers to a gene which differs from MCP-1 with respect to base sequence but which displays relatively high homology to MCP-1 and has the same or similar activity to that of MCP-1. Here, the homology is not particularly limited so long as the functional equivalency exists, but the homology of base sequence is preferably 70-100%, more preferably 80-100%, and most preferably 90-100%. If the homology is less than the lower limit, the possibility of the gene not displaying the same or similar function to that of MCP-1 tends to be high. However, even if the homology of base sequence is less than the lower limit, the gene may sometimes have the same or similar function to that of MCP-1 when the domain having the function characteristic of MCP-1 is highly homologous to the base sequence corresponding to the domain. Such gene can preferably be used although its homology of base sequence is outside the aforementioned range. The gene having relatively high homology may be a gene having a substitution, a deletion, an addition and/or an insertion at one or two or more bases in the MCP-1 gene naturally or artificially.

If the administration or contacting of the compound to be assayed is conducted, the expression level of the MCP-1 gene or the gene that is functionally equivalent thereto will be lowered by not less than 5%, preferably not less than 10%, more preferably not less than 20% as compared to where neither administration nor contacting of the compound to be assayed is conducted. In this case, the compound to be assayed can be evaluated to be effective for the treatment or prevention of obesity. On the other hand, if the administration or contacting of the compound to be assayed is conducted, the expression level of the MCP-1 gene or the gene that is functionally equivalent thereto will be elevated by not less than 5%, preferably not less than 10%, more preferably not less than 20% as compared to where neither administration nor contacting of the compound to be assayed is conducted. In this case, the compound to be assayed can be evaluated to be effective for the treatment or prevention of leanness.

(B) Method for Evaluation Using as an Index, the Ability to Modulate the Expression Level of the MCP-1 Protein A compound to be assayed is administered to or contacted with an animal or cell subject to establish whether the compound modulates the expression level of the MCP-1 protein or a protein that is functionally equivalent thereto in the animal or cell subject. This allows the evaluation of an effective compound for the treatment or prevention of obesity or leanness.

The methods of administering to or contacting with the animal or cell subject the compound to be assayed are the same as the techniques as described for the method of evaluation as an index, the ability to modulate the expression level of the MCP-1 gene.

The method of establishing the presence or the absence of modulation of the expression level of the protein is not particularly limited. The method can be performed by detecting any change in the expression amount of the protein as the control being prior to the administration or the contacting, according to the technique utilizing a protein chip (e.g., a protein chip system manufactured by Ciphergen Biosystems Ltd.), or an immunological technique (e.g., ELISA, EIA or Western blotting). Measurement of blood concentration of the MCP-1 protein is preferably carried out to establish the presence or the absence of modulation of the expression level of the protein.

Herein, "protein that is functionally equivalent to the MCP-1 protein" refers to a protein which differs from the MCP-1 protein with respect to amino acid sequence but which displays relatively high homology to the MCP-1 protein and has the same or similar activity to that of the MCP-1 protein. Here, the homology is not particularly limited so long as the functional equivalency exists, but the homology of amino acid sequence is preferably 50-100%, more preferably 60-100%, and most preferably 70-100%. If the homology is less than the lower limit, the possibility of the protein not displaying the same or similar function to that of the MCP-1 protein tends to be high. However, even if the homology of amino acid sequence is less than the lower limit, the protein may sometimes have the same or similar function to that of the MCP-1 protein when the amino acid sequence of a domain having the function characteristic of the MCP-1 protein is highly homologous to the amino acid sequence of the protein corresponding to the domain. Such protein can preferably be used although its homology of amino acid sequence is outside the aforementioned range. The protein with relatively high homology may be a protein having a substitution, a deletion, an addition and/or an insertion at one or two or more amino acid residues in the MCP-1 protein naturally or artificially.

If the administration or contact of the compound to be assayed is conducted, the expression level of the MCP-1 protein or the protein that is functionally equivalent thereto will be lowered by not less than 5%, preferably not less than 10%, more preferably not less than 20% as compared to where neither administration nor contact of the compound to be assayed is conducted. In this case, the compound to be assayed can be evaluated to be effective for the treatment or prevention of obesity. On the other hand, if the administration or contact of the compound to be assayed is conducted, the expression level of the MCP-1 protein or the protein that is functionally equivalent thereto will be elevated by not less than 5%, preferably not less than 10%, more preferably not less than 20% as compared to where neither administration nor contact of the compound to be assayed is conducted. In this case, the compound to be assayed can be evaluated to be effective for the treatment or prevention of leanness.

(C) Method of Evaluation Using as an Index, the Activity of the MCP-1 Protein

A compound to be assayed is contacted with the MCP-1 protein to establish whether the compound influences the activity of the MCP-1 protein. This allows the evaluation of an effective compound for the treatment or prevention of obesity or leanness.

Specifically, the evaluation of a compound to be assayed is carried out in the procedure below.

The compound to be assayed is first contacted with the MCP-1 protein.

The method of contacting the compound to be assayed with the protein as described above is not particularly limited. Specifically, there is a method of mixing them in a solution such as a buffer (phosphate buffer or the like) to allow contacting, for example.

Next, it is established whether the compound to be assayed influences the activity of the MCP-1 protein. The conditions for the determination of the protein activity may be appropriately set depending on the properties of the protein to be used. These conditions are specifically such that the chemotaxis ability of monocytes can be an index in the case of the MCP-1 protein. For example, the determination can be carried out by referring to J. Clin. Invest. 90, 772-779 (1992); Kidney Int. 44, 1036-1047 (1993).

If the contacting of the compound to be assayed with the MCP-1 protein is conducted, the activity of the MCP-1 protein will be lowered by not less than 5%, preferably not less than 10%, more preferably not less than 20% as compared to where the compound to be assayed is not contacted with the MCP-1 protein. In this case, the compound to be assayed can be evaluated to be effective for the treatment or prevention of obesity. On the other hand, if the compound to be assayed is contacted with the MCP-1 protein, the activity of the MCP-1 protein will be elevated by not less than 5%, preferably not less than 10%, more preferably not less than 20% as compared to where the compound to be assayed is not contacted with the MCP-1 protein. In this case, the compound to be assayed can be evaluated to be effective for the treatment or prevention of leanness.

As described above, based on the method for evaluating a compound to be effective for the treatment or prevention of obesity or leanness according to this invention, it will be possible to perform the screening for therapeutic or diagnostic agents for obesity or leanness, the evaluation of these agents for their effectiveness or safety and the selection of suitable agents in the tailored medication.

(4) Effective Compounds for the Treatment or Prevention of Obesity or Leanness According to this Invention Since the involvement of MCP-1 in obesity and body weight changes has been elucidated, the compounds that have been evaluated effective by the evaluation methods described above are extremely useful as therapeutic or preventive agents for obesity or leanness.

EXAMPLES

This invention will be described in more details by referring to examples; however, the invention is not to be limited to the following examples.

(Construction of Obesity Model Animals)

Preparation Example 1

(Mice i.c.v. administered with Neuropeptide Y (NPY) Y5 Agonist)

Model mice displaying obesity were constructed by the administration of NPY Y5 agonist in the manner described below.

Male mice (9-12 weeks old) (C57BL/6J, CLEA, Inc.) were bred at one animal per plastic cage under the conditions of: room temperature 23±2° C.; and humidity 55±15%. The light-dark cycle during breeding period was set to be 12 hours and the light was put on at 7 a.m. and turned off at 7 p.m. Mice were allowed access to ad lib feed (CE-2 (protein: 25.4 wt. %; carbohydrate: 50.3 wt. %; lipid: 4.4 wt. %), CLEA, Inc.) and water.

Mice were anesthetized with 80 mg/kg of sodium pentobarbital (Dinabott Inc.) and were locally implanted with sterilized 28-gage brain fusion cannulas (Alzet) at their right cerebral ventricles. The cannula was fixed vertically relative to the cranical bone at the position 0.4 mm behind and 0.8 mm side of the bregma and 2 mm deep. The cannula was fixed to the ventricle with dental cement. The cannula was connected to an osmotic pump (model no. 2002 manufactured by Alzet) filled with 10 mM phosphate buffer containing 0.05% bovine serum albumin via a polyvinylchloride tube. After the pump was filled with a solution of D-Try$^{34}$ NPY (adjusted to 5 µg/day) dissolved in 10 mM PBS containing 0.05% BSA, it was implanted subcutaniously at the back of the mice and the mice were subcutaneously injected with an antibiotic (50 mg/kg of cefamedine manufactured by Fujisawa Pharmaceutical Co. Ltd.).

These mice were divided into three groups for which average weights were evenly matched: a group (vehicle group) into which only solvent was infused; a group (ad lib fed group) into which D-Try$^{34}$ NPY (NPY Y5 agonist) was infused; and a group (pair-fed group) into which D-Try$^{34}$ NPY was infused and which was pair-fed.

Preparation Example 2

(DIO (Diet-Induced Obesity) Mice)

Mice of 18 weeks old (C57BL/6J, CLEA, Inc.) were bred at one animal per plastic cage under the conditions of: room temperature 23±2° C.; and humidity 55±15%. The mice were fed with a high-calorie diet MHF (protein: 18.2 wt. %; carbohydrate: 55.6 wt. %; lipid: 15.5 wt. %) over 6 months and model mice displaying obesity (DIO mice) were constructed. In the Examples, "established MFD" refers to a mouse that was fed with MHF until no more weight gain was noted.

The above mice were offered a high-calorie diet HFD (protein: 20.8 wt. %; carbohydrate: 38.59 wt. %; lipid: 32.88 wt. %), which contains more fat than MHF and DIO mice (HFD) were constructed.

Preparation Example 3

(Fasted Mice)

Mice (17 weeks old, C57BL/6N) were bred individually at one animal per cage. Regular diet (CA-1, CLEA) was offered.

Fasting was carried out in the schedule described below. Specifically, the animals were offered feed (CA-1) only for 3 hours (10:00 to 13:00) in a day and allowed access to ad lib water. The weight of the feed was weighed before and after feeding time and the difference was taken as intake amount. Body weight, observation on appearance and the like were monitored during the fasting period. The mice that had been regarded failure in conditioning (the mice displaying an extreme body weight loss during a short period (e.g., a loss on the order of 20%)) were not used in the experiment. After the mice were bred for 7 days under such conditions, white adipocytes were extracted from the animals.

Examples 1-3 and Comparative Example 1

(Expression of MCP-1 in White Adipocytes)

The quantitative analysis of the expression amount of MCP-1 was performed by TaqMan PCR, using cDNA obtained from the white adipocytes according to RT-PCR. The standard curve was prepared using a mouse MCP-1 cDNA fragment (Accession No. NM011333) and calibrated based on the expression amount of β-actin. The base sequences of the primers used are shown:
Mouse MCP-1 TaqMan Probe: 5'-CCA CTC ACC TGC TGC TAC TCA TTC ACC A-3' (SEQ NO:1)
mMCP1-69F: 5'-TCA GCC AGA TGC AGT TAA CGC-3' (SEQ NO:2)
mMCP1-163R: 5'-TGA TCC TCT TGT AGC TCT CCA GC-3' (SEQ NO:3)
Mouse β-actin TaqMan Probe: 5'-CCT GAG GCT CTT TTC CAG CCT TCC TTC T-3' (SEQ NO:4)
mMCP1-F: 5'-TAT TGG CAA CGA GCG GTT C-3' (SEQ NO:5)
mMCP1-R: 5'-ATG CCA CAG GAT TCC ATA CCC-3' (SEQ NO:6)

Primers for the Construction of Mouse MCP-1 cDNA Fragment
mMCP1-26F: 5'-CCT GCT GTT CAC AGT TGC C-3' (SEQ NO:7)
mMCP1-440R: 5'-CAC TGT CAC ACT GGT CAC TCC-3' (SEQ NO:8)

When the expression amounts of MCP-1 and leptin in non-treated C57BL/6N white adipocytes are respectively set to be 1, the expression amounts of these genes in the DIO mice (DIO), the D-Try$^{34}$NPY administered mice (Y5 agonist FF), the D-Try$^{34}$NPY (pair feeding) administered mice (Y5 agonist PF) and the fasted mice groups are shown in Table 1. Table 1 clearly shows that the expression amount of MCP-1 was elevated in the obesity model mice and lowered in the fasted mice. Accordingly, it has become clear that the expression amount of MCP-1 and body weight bear a correlation.

TABLE 1

|  | Obesity model | Expression amount of MCP-1 | Expression amount of leptin |
|---|---|---|---|
| Example 1 | Y5 agonist PF | 5.16 | 1.77 |
| Example 2 | Y5 agonist FF | 7.67 | 3.53 |
| Example 3 | DIO mice | 7.64 | 3.06 |
| Comparative Example 1 | Fasting | 0.28 | 0.28 |

Example 4

(Blood Concentrations of MCP-1 in the Obesity Model Mice)

The blood concentrations of MCP-1 in the DIO mice were measured and the relationship between obesity and the MCP-1 concentrations were examined. Measurement of the MCP-1 blood concentration in each mouse was performed in the manner as described below.

The DIO mice (55 animals) were fed with MHF from 8 weeks old and blood was collected from the tail vein of the animals at the age of 15 weeks. These plasma components were used to measure the blood concentrations of MCP-1. Specifically, the heparin-added blood collection from the mouse tail vein was carried out and the plasma component was collected by centrifugation. Next, 50 μl of the plasma was incubated in an antibody-immobilized plate at room temperature for 2 hours. After this plate was washed with buffer, an anti-mouse MCP-1 antibody labeled with enzyme was added thereto and the plate was incubated at room temperature for additional 2 hours. After washing the plate with buffer again, an enzyme substrate solution was added thereto and the plate was incubated at room temperature for 30 minutes in the dark. After this reaction was stopped with hydrochloric acid, absorbance was measured. A standard curve was prepared from the absorbance data of the MCP-1 solution for the curve and the MCP-1 concentrations in the plasma were thus determined (EIA sandwich assay, R&D System Co., Ltd.).

Figure 2:
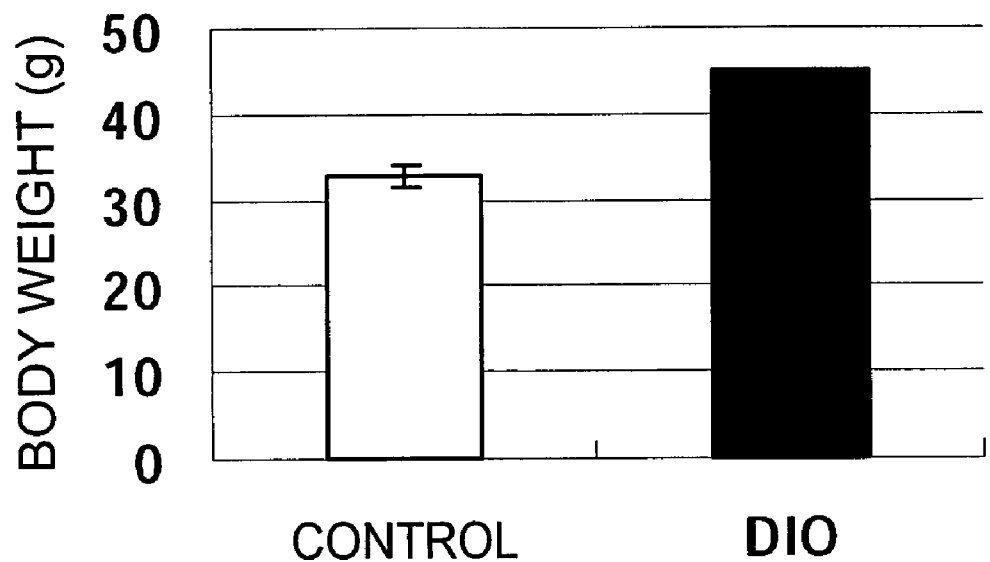
FIG. 2 is a graph comparing the body weights between DIO mice and the control group.

As shown in FIG. 1, it was understood that the blood concentration of MCP-1 was markedly elevated in the DIO mice as compared to the control group (C57BL/6N). The body weight difference between the DIO mice used and those in the control group is shown in FIG. 2.

Figure 3:
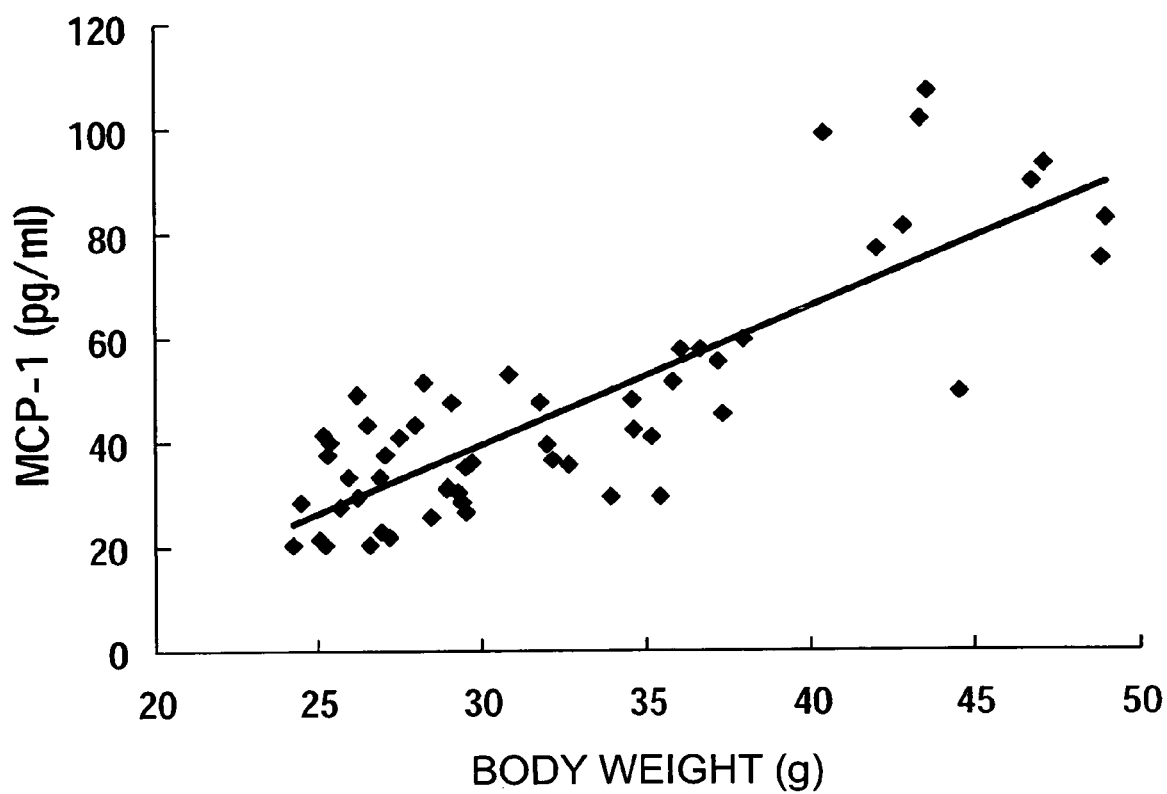
FIG. 3 is a graph showing the relationship between the body weights and the blood concentrations of MCP-1 in DIO mice.

FIG. 3 shows the relationship between the body weights of the DIO mice and the blood concentrations of MCP-1. As is apparent from FIG. 3, it was found that a certain correlation existed between the blood concentrations of MCP-1 and the body weights.

Example 5

(Expression of MCP-1 in the White Adipocytes of Fasted Model Mice)

The fasted model mice constructed in Example 3 were used to determine the expression amounts of MCP-1. Here, the determination of the expression amounts of MCP-1 was conducted similarly to Example 1.

Figure 4:
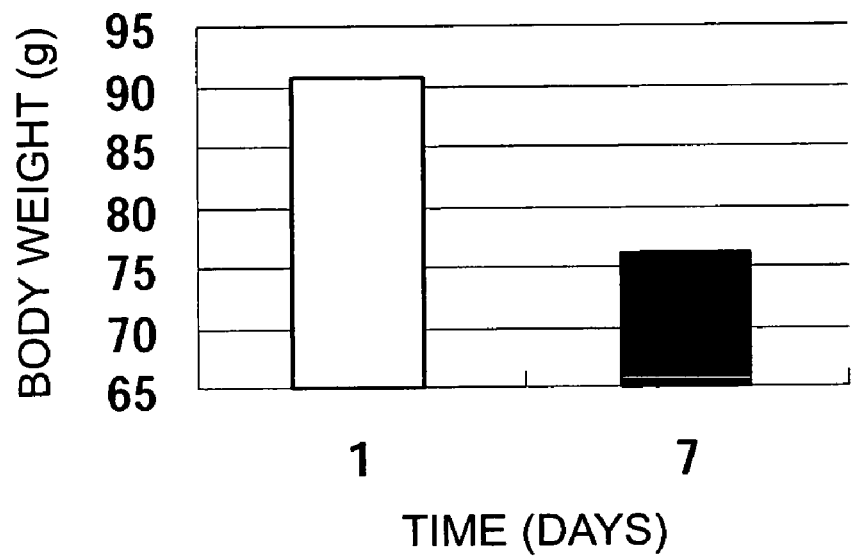
FIG. 4 is a graph comparing the body weights of model mice before and after fasting.

FIG. 4 shows a body weight change before and after fasting in the model mice. In FIG. 4 the ordinate represents the body weight after fasting relative the body weight before fasting as expressed in percentage.

Figure 5:
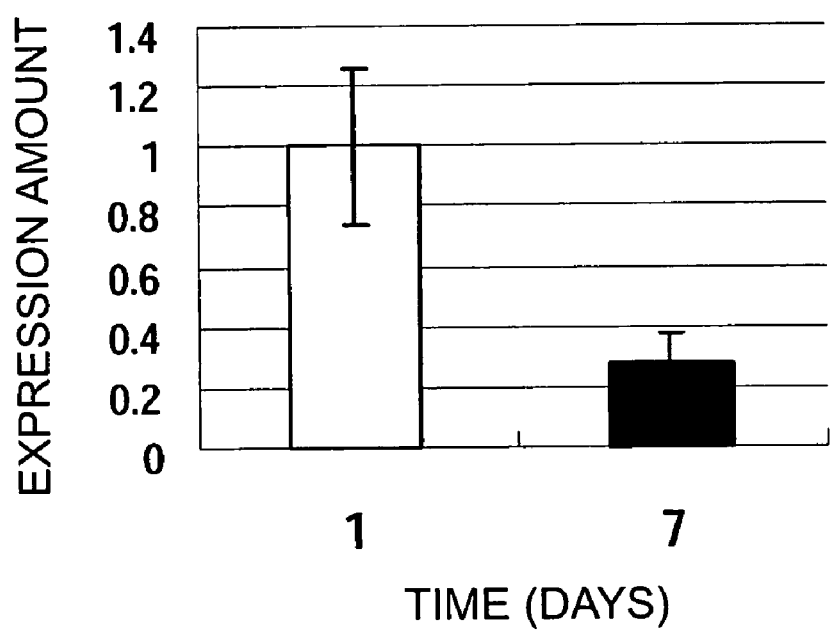
FIG. 5 is a graph comparing the expression levels of MCP-1 in the white adipocytes of model mice before and after fasting.

FIG. 5 shows the expression amounts of MCP-1 in the model mice before and after fasting. As is apparent from FIG. 5, the fasting markedly decreased the expression amount of MCP-1. Here in FIG. 5, the ordinate represents the expression amount of MCP-1 when the expression amount of MCP-1 before fasting was taken as "1."

As described above, it has become clear that there is a close correlation between the body weight decrease and the expression amount of MCP-1.

Example 6

(Blood Concentrations of MCP-1 in Fasted Model Mice)

The fasted model mice constructed in Example 3 were used to determine the blood concentrations of MCP-1. The determination of the blood concentrations of MCP-1 was conducted similarly to Example 4.

Figure 6:
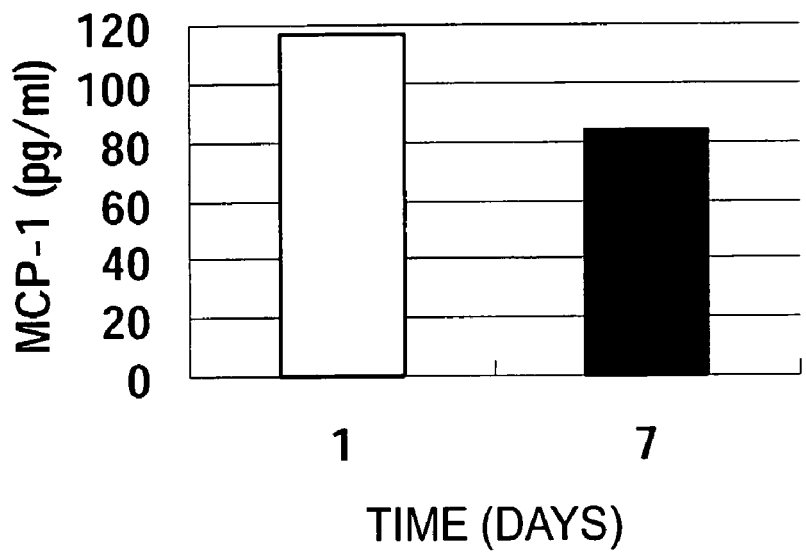
FIG. 6 is a graph comparing the blood concentrations of MCP-1 in model mice before and after fasting.

As is apparent from FIG. 6, the blood concentration of MCP-1 was markedly lowered after fasting as compared to before fasting. This has made it clear that there is a close correlation between the body weight decrease and the concentration of MCP-1.

Examples 7-9

(Variations in the Expression Amount and the Blood Concentration of MCP-1 by Administration of a Compound Having Obesity-Suppressing Action)

Figure 7:
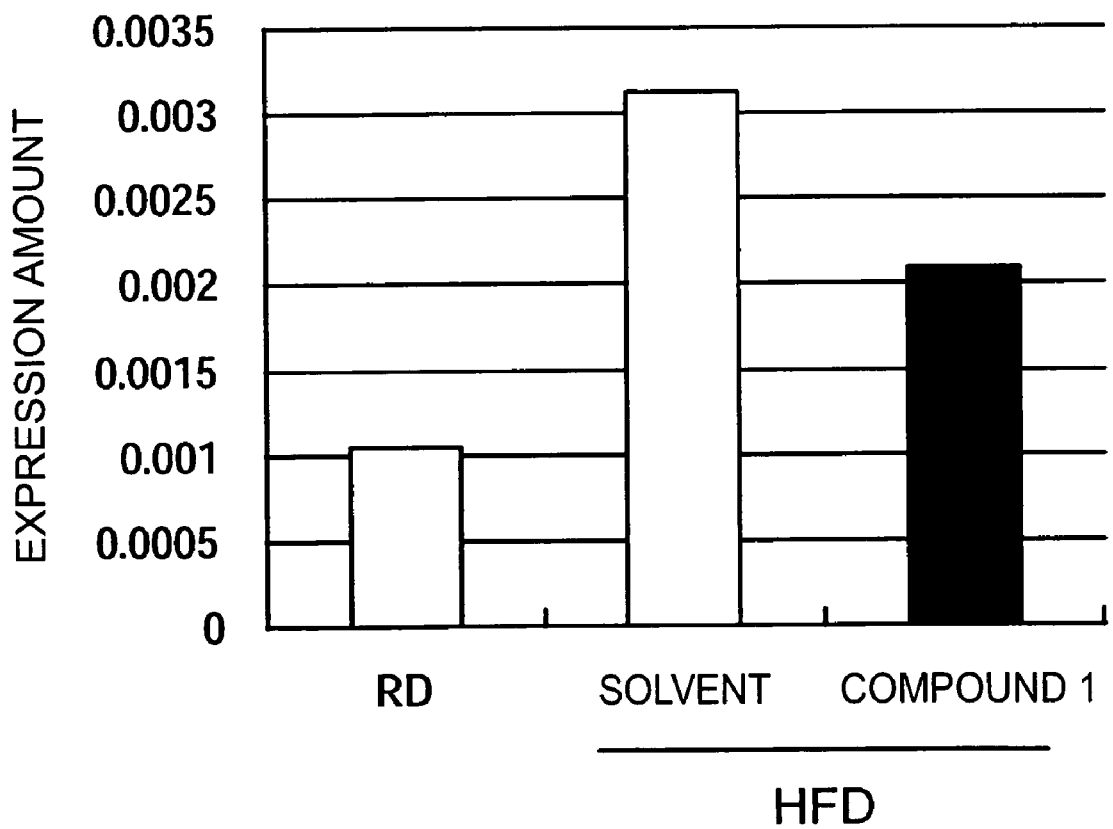
FIG. 7 is a graph showing the relationship between the administration of an obesity-suppressing compound and the expression amounts of MCP-1 in DIO mice.

After DIO mice (HFD) were administered with the compound having obesity-suppressing action as described in WO01/14376 (Compound 1), the expression amounts of MCP-1 in white adipocytes of the mice were determined. As shown in FIG. 7, the expression of MCP-1 was markedly elevated in the DIO (HFD) mice, whereas the expression was significantly lowered when the mice were administered with the compound having obesity-suppressing action (Example 7). Here in FIG. 7, RD represents the mice fed with regular diet and the ordinate represents values obtained by calibrating the expression amounts of mRNA with the expression amount of β-actin.

Figure 8:
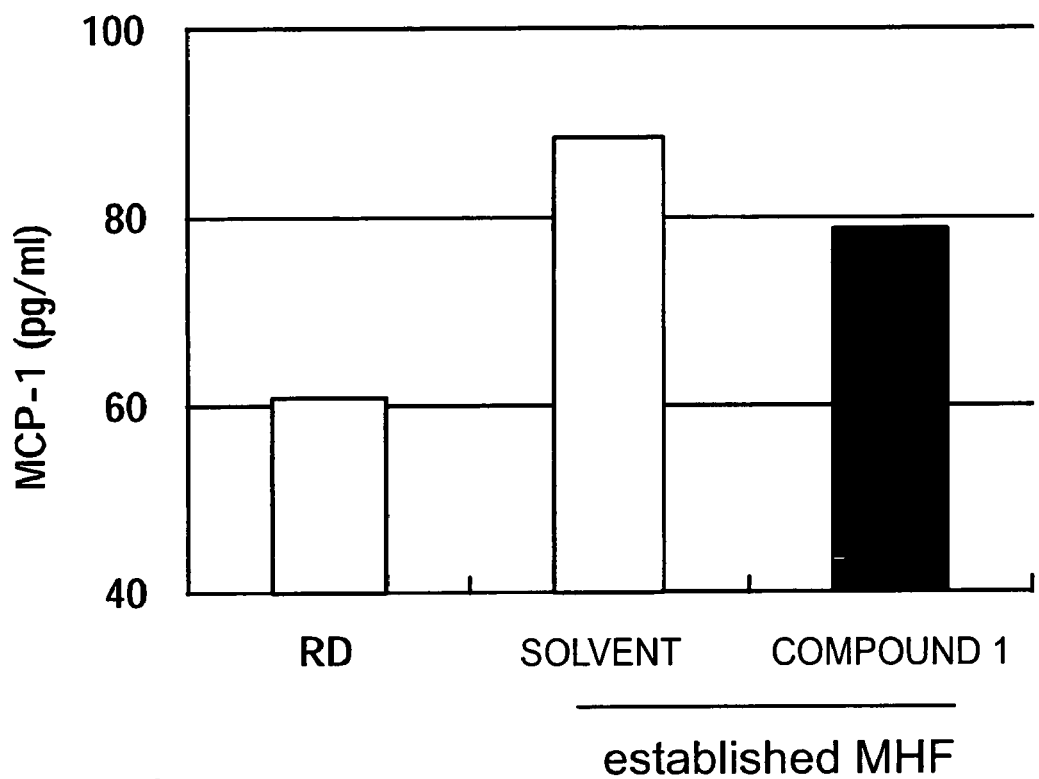
FIG. 8 is a graph showing the relationship between the administration of an obesity-suppressing compound and the blood concentrations of MCP-1 in DIO mice.

After DIO mice were also administered with the compound having obesity-suppressing action as described in WO01/14376 (Compound 1), the blood concentrations of MCP-1 were measured. As shown in FIG. 8, the blood concentration of MCP-1 was markedly elevated in the DIO (MHF) mice, whereas the blood concentration was significantly lowered when the mice were administered with the compound having obesity-suppressing action (Example 8).

Figure 9:
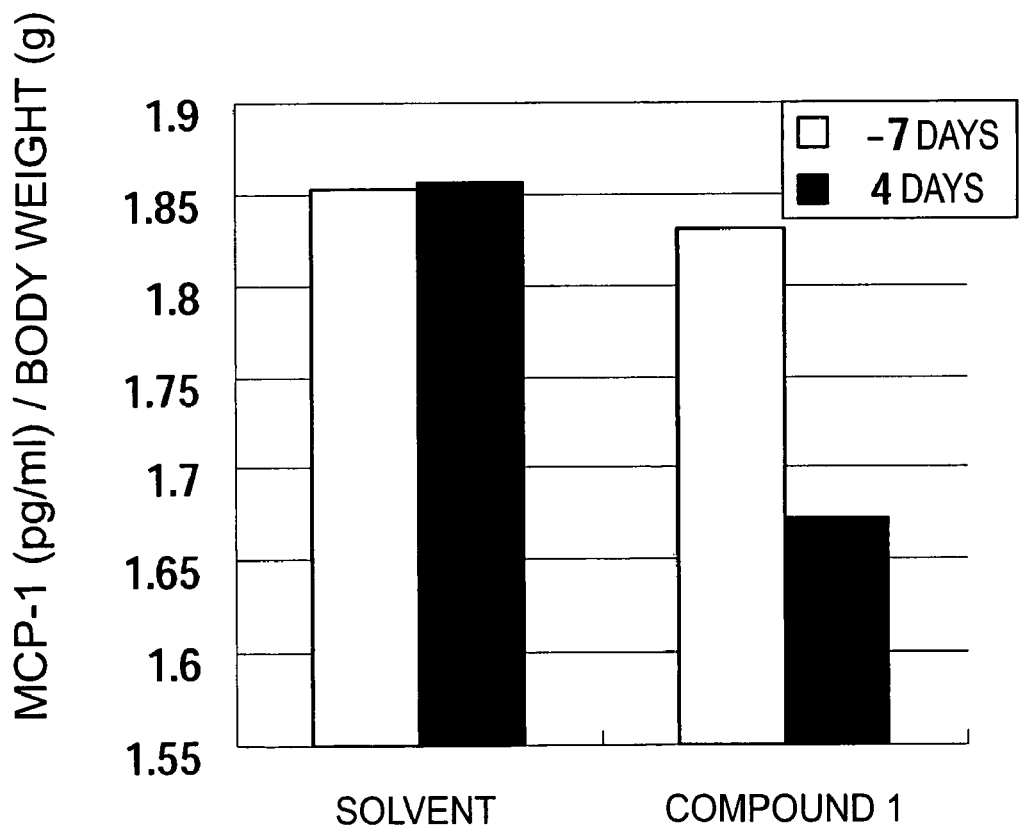
FIG. 9 is a graph showing the relationship between the administration of an obesity-suppressing compound and the blood concentrations of MCP-1 before and after fasting.
Figure 10A:
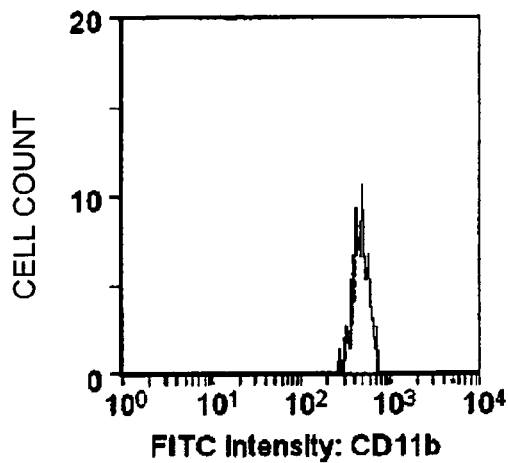
FIGS. 10(A), 10(B), 10(D) and 10(E) are respective graphs showing the fluorescence intensity of CD11b and the cell counts for different cells. (C) and (F) are graphs showing the CD11 positive cell counts of different cells.
Figure 10B:
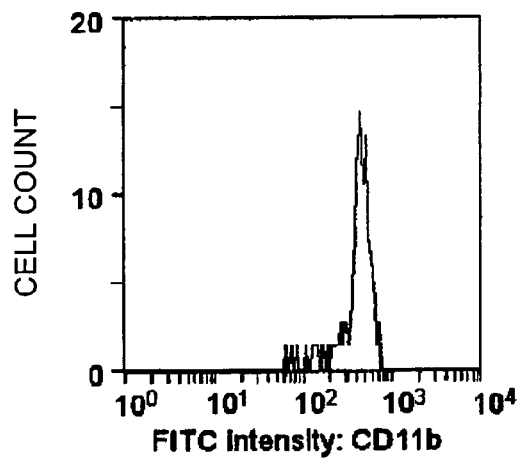
Figure 10C:
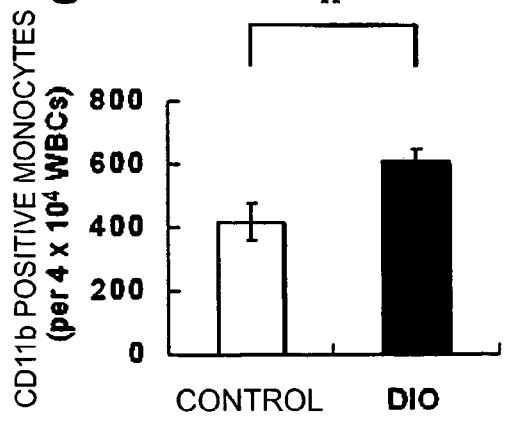
Figure 10D:
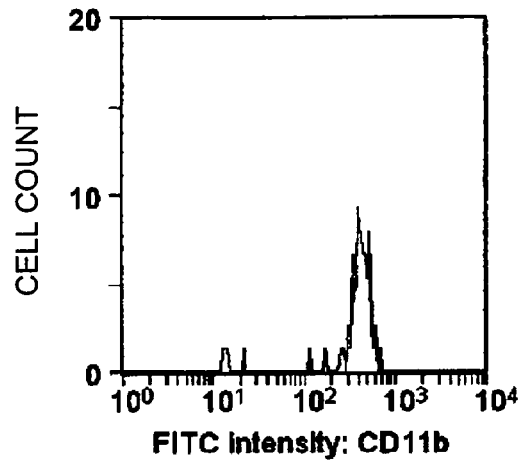
Figure 10E:
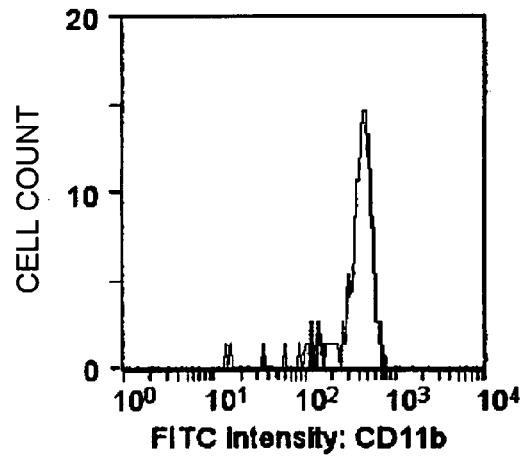
Figure 10F:
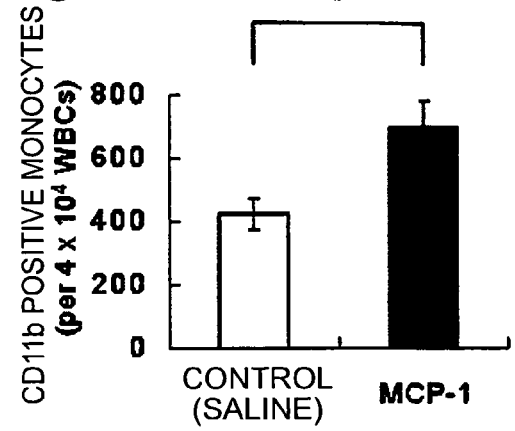

In addition, on the 4th day after DIO mice were administered with the compound, blood was collected and the blood concentrations of MCP-1 were determined and normalized with their body weights. As shown in FIG. 9, the blood concentration was lowered on the 4th day although the body weight did not decrease. This indicates that the decrease in the blood concentration of MCP-1 occurs prior to the decrease in body weight (Example 9). Further, on the 4th day of administration of the compound the expression of the MCP-1 gene was lowered whereas the expression of the leptin gene showed no change. This has made it clear that MCP-1 responds to the body weight change before leptin.

Example 10

(Expression Analysis of CD11b by Flow Cytometry)

The analysis using flow cytometry was performed to study how the count of CD11b, which was a surface antigen of macrophages, or blood monocytes would vary upon administration of MCP-1.

Mice were first subcutaneously infused with. MCP-1, using an osmotic pump, at the rate of 10 ng/0.5 μl/hr over 2 weeks. Next, blood was collected from the tail veins of the control mice (C57BL/6), the DIO mice and the MCP-1 treated mice, respectively, using a heparinized capillary. After blood cells were collected from the blood by centrifugation at 300×g for 5 minutes, they were incubated with the FITC-labeled anti-mouse CD11b antibody (BD Biosciences) at room temperature for 15 minutes. The samples were incubated with the IgG2b isotype to serve as a non-specific binding control. After washing these cells with PBS, erythrocytes were lyzed with a lysis buffer at room temperature for 5 minutes. After washing the cells with PBS, the cells were suspended in PBS containing 0.5% formaldehyde. Flow cytometry was performed on this suspension, using an EPCIS Elite Flow Cytometer (Beckman Coulter, Inc.), to identify monocytes. Here, the analysis by flow cytometry was carried out by determining the population of monocytes/macrophages in the whole blood cells. In the flow cytometry 40,000 cells per each sample were analyzed with the fluorescence and scattered light as indices.

The results from the flow cytometry are shown in FIGS. 10($a$) to 10($f$). Here, FIG. 10($a$) shows the results of the blood cells derived from the control mice. FIG. 10($b$) shows the results of the blood cells derived from the DIO mice. FIG. 10($c$) shows the counts of CD11b positive monocytes in the control mice and the DIO mice. FIG. 10($d$) shows the results of the blood cells derived from the control mice administered with saline. FIG. 10($e$) shows the results of the blood cells derived from the mice administered with MCP-1. FIG. 10($f$) shows the counts of CD11b positive blood cells in the saline-administered control mice and the MCP-1 administered mice. FIG. 10($a$) to 10($f$) could confirm increases in the CD11b positive blood cell count, i.e., the number of macrophages, in the DIO mice and the mice externally administered with MCP-1. It is thus thought that the increase in CD11b positive monocytes accelerates the chemotaxis of the monocytes to the arteriosclerotic lesion. In other words, it has been verified that not only MCP-1 secreted from the vascular endothelium, but also MCP-1 externally administered causes the chemotaxis of the monocytes.

INDUSTRIAL APPLICABILITY

The method for examination according to this invention will enable the examination or prediction of obesity or leanness at a molecular level, and more accurate diagnoses than conventional diagnostic methods will thus be feasible. The method for evaluating a compound according to this invention will enable various kinds of evaluations such as screening for therapeutic or diagnostic agents for obesity or leanness.

What is claimed is:

1. A method of evaluating body mass in a mouse comprising:
   i) obtaining an adipose tissue sample from the mouse;
   ii) isolating mRNA from the sample;
   iii) analyzing said mRNA to determine the quantity of MCP-1 mRNA of SEQ ID NO. 11; and
   iv) determining that said mouse has a propensity for increased body mass if there is at least a 500% increase in the level of MCP-1 mRNA of SEQ ID NO: 11 relative to a control, or a propensity for decreased body mass if there is a least a 70% decrease in the level of MCP-1 mRNA of SEQ ID NO: 11 relative to a control.

* * * * *